(12) United States Patent
Kontothanassis et al.

(10) Patent No.: US 7,734,335 B2
(45) Date of Patent: Jun. 8, 2010

(54) METHOD AND APPARATUS FOR IMPROVING THE ACCURACY OF ATRIAL FIBRILLATION DETECTION IN LOSSY DATA SYSTEMS

(75) Inventors: Leonidas Kontothanassis, Arlington, MA (US); Beth Logan, Cambridge, MA (US); David Goddeau, Watertown, MA (US)

(73) Assignee: Hewlett-Packard Development Company, L.P., Houston, TX (US)

( * ) Notice: Subject to any disclaimer, the term of this patent is extended or adjusted under 35 U.S.C. 154(b) by 908 days.

(21) Appl. No.: 11/241,294

(22) Filed: Sep. 29, 2005

(65) Prior Publication Data

US 2007/0073177 A1    Mar. 29, 2007

(51) Int. Cl.
- A61B 5/0402   (2006.01)
- A61B 5/0468   (2006.01)
- A61B 5/0452   (2006.01)
- A61B 5/046    (2006.01)

(52) U.S. Cl. .................. 600/515; 600/516; 600/519
(58) Field of Classification Search ............... 600/509, 600/515, 516, 519
See application file for complete search history.

(56) References Cited

U.S. PATENT DOCUMENTS

| | | | |
|---|---|---|---|
| 5,464,431 A | 11/1995 | Adams et al. | |
| 5,694,941 A | 12/1997 | Riley | |
| 5,730,142 A * | 3/1998 | Sun et al. | 600/578 |
| 6,701,183 B2 | 3/2004 | Baker et al. | |
| 6,826,425 B2 | 11/2004 | Bardy | |
| 6,871,089 B2 | 3/2005 | Korzinov et al. | |
| 6,879,856 B2 | 4/2005 | Stadler et al. | |
| 2004/0010201 A1 * | 1/2004 | Korzinov et al. | 600/518 |
| 2005/0165320 A1 | 7/2005 | Glass et al. | |
| 2006/0276716 A1 * | 12/2006 | Healey et al. | 600/516 |

(Continued)

FOREIGN PATENT DOCUMENTS

WO    WO 2005/067790    7/2005

OTHER PUBLICATIONS

International Search Report for SN PCT/US2006/038089 dated Jun. 12, 2007 (5 pages).

(Continued)

*Primary Examiner*—Carl H. Layno
*Assistant Examiner*—Tammie K Heller (57) ABSTRACT

An apparatus and a method for detecting cardiac atrial fibrillation events in an EKG signal. The method comprises the steps of detecting a portion of an EKG signal comprising cardiac beats; measuring the duration of a gap in the detected portion of the EKG signal; and computing two or more inter-beat intervals. The computed interval is outputted if the gap in the portion of the EKG signal is not more than a fraction alpha of the computed interval. The method further includes the steps of computing the variance of the inter-beat intervals and classifying the portions of the EKG signal as indicative of an atrial fibrillation event. During classification, the inter-beat interval variance of the portion of the EKG signal that exceeds a pre-determined value V is indicative of an atrial fibrillation event. The method further includes discarding portions of the EKG signal classified as indicative of atrial fibrillation if said portions have a duration less than a pre-determined threshold S and annotating the EKG signal. The non-discarded portions of the EKG signals having inter-beat variances that exceed V are annotated as atrial fibrillation events.

26 Claims, 5 Drawing Sheets

U.S. PATENT DOCUMENTS

2007/0010752 A1* 1/2007 Korhonen .................. 600/516

OTHER PUBLICATIONS

Moody, G.B. and R.G. Mark, "A New Method for Detecting Atrial Fibrillation Using R-R Intervals," *Computers in Cardiology 1983*, pp. 227-230.

Babcock, B. et al., "Load Shedding for Aggregation Queries over Data Streams," *Proceedings 20th International Conference on Data Engineering*, Mar. 30, 2004-Apr. 2, 2004, pp. 350-361.

Abadi, D.J., "The Design of the Borealis Stream Processing Engine," *Proceedings of the 2005 CIDR Conference*, pp. 277-289.

Reiss, F. and J.M. Hellerstein, "Data Triage: An Adaptive Architecture for Load Shedding in TelegraphCQ," *Proceedings of the 21st International Conference on Data Engineering (ICDE 2005)*, (2 pp.)

* cited by examiner

METHOD AND APPARATUS FOR IMPROVING THE ACCURACY OF ATRIAL FIBRILLATION DETECTION IN LOSSY DATA SYSTEMS

BACKGROUND OF THE INVENTION

Continuous physiological monitoring can play a crucial role in finding and treating asymptomatic pathologies in patients before they become life threatening. Examples of useful physiological data that can be collected and analyzed include electrocardiograms (EKG), blood oxygen levels, weight, blood pressure and many others.

In a typical continuous monitoring system, patients wear devices that collect data of interest continuously and the data is aggregated and transmitted to a remote host for further analysis. Settings like this are of particular interest for diseases like Atrial Fibrillation (Afib) which are both asymptomatic and intermittent. Continuous monitoring using wearable EKG's can provide the information necessary to diagnose and treat the disease.

Unfortunately, in the typical monitoring environment, a variety of factors conspire to reduce the quality of the signal. Noise due to patient mobility, packet loss due to wireless problems, aggregating device buffer overruns and other problems result in losing some fraction of the data being collected by the device. There is a need in a method and a device for detecting atrial fibrillation events in a signal transmitted in a lossy data stream.

SUMMARY OF THE INVENTION

The present invention is a method and an apparatus for detecting atrial fibrillation events in an EKG signal that is transmitted in a lossy data stream. Vastly better results are achieved than the prior art R-R based approaches even for data loss rates as high as 30%.

In one embodiment, the present invention is a method of detecting a cardiac atrial fibrillation event in an EKG signal. The method comprises: detecting a portion of an EKG signal comprising cardiac beats; measuring the duration of a gap in the detected portion of an EKG signal; and computing two or more inter-beat intervals. The computed interval is outputted if the gap in the portion of the EKG signal is not more than a fraction alpha of the computed interval. The method further includes computing the variance of the inter-beat intervals and classifying the portions of the EKG signal as indicative of an atrial fibrillation event. During classification, the inter-beat interval variance of the portion of the EKG signal that exceeds a pre-determined value V is indicative of an atrial fibrillation event. The method further includes discarding portions of the EKG signal classified as indicative of atrial fibrillation if said portions have a duration less than a pre-determined threshold S, and annotating the EKG signal. The non-discarded portions of the EKG signals having inter-beat variances that exceed V are annotated as atrial fibrillation events.

In another embodiment, the present invention is a method of detecting a cardiac atrial fibrillation event in an EKG signal data stream that comprises time-stamped packets. The method comprises detecting a portion of an EKG signal comprising cardiac beats; comparing the time-stamp of each packet to an expected time-stamp, thereby measuring the duration of a gap in the portion of the EKG signal data stream; and computing two or more inter-beat intervals (intervals between cardiac beats). The computed interval is outputted if the gap in the portion of the EKG signal is not more than a fraction alpha of the computed interval. The method further includes computing the variance of the intervals between cardiac beats for a pre-determined number of cardiac beats N if no interval is greater than a predetermined time T, and classifying the portions of the EKG signal as indicative of an atrial fibrillation event. During classification, the inter-beat interval variance of the portion of the EKG signal that exceeds a pre-determined value V is indicative of an atrial fibrillation event. The method further includes discarding portions of the EKG signal classified as indicative of atrial fibrillation if said portions have a duration less than a pre-determined number of beats M, and annotating the EKG signal. During annotation, the non-discarded portions of the EKG signals having inter-beat variances that exceed V are annotated as atrial fibrillation events.

In another embodiment, the present invention is an apparatus for detecting a cardiac atrial fibrillation event in an EKG signal. The apparatus comprises means for detecting a portion of an EKG signal comprising cardiac beats; means for measuring the duration of a gap in the portion of the EKG signal; and means for computing inter-beat intervals. The computed interval is outputted if the gap in the portion of the EKG signal is not more than a fraction alpha of the computed interval. The apparatus further includes means for computing the variance of the inter-beat intervals (inter-beat variance) and means for classifying the portions of the EKG signal as indicative of an atrial fibrillation event. The inter-beat variance of the portion of the EKG signal that exceeds a pre-determined value V is indicative of an atrial fibrillation event. The apparatus further includes means for discarding portions of the EKG signal classified as indicative of atrial fibrillation if said portions have a duration less than a pre-determined threshold S and means for annotating the EKG signal. The non-discarded portions of the EKG signals having inter-beat variances that exceed V are annotated as atrial fibrillation events.

In another embodiment, the present invention is an apparatus for detecting a cardiac atrial fibrillation event in an EKG signal data stream that comprises time-stamped packets. The apparatus comprises means for detecting a portion of an EKG signal comprising cardiac beats; means for comparing the time-stamp of each packet to an expected time-stamp, and thereby measuring the duration of a gap in the EKG signal data stream; and means for computing inter-beat intervals. The computed interval is outputted if the gap in the portion of the EKG signal is not more than a fraction alpha of the computed interval. The apparatus further includes means for computing the variance of the inter-beat intervals (inter-beat variance) for a pre-determined number of cardiac beats N, said means computing the variance if no interval is greater than a predetermined time T, and means for classifying the portions of the EKG signal as indicative of an atrial fibrillation event. The inter-beat variance of the portion of the EKG signal that exceeds a pre-determined value V is indicative of an atrial fibrillation event. The apparatus further includes means for discarding portions of the EKG signal classified as indicative of atrial fibrillation if said portions have a duration less than a number of beats M, and means for annotating the EKG signal. The non-discarded portions of the EKG signals having inter-beat variances that exceed V are annotated as atrial fibrillation events.

The present invention can be adapted for use with any "R-R" based atrial fibrillation detection algorithm. Vastly better results are achieved by the method and apparatus of the present invention when compared the prior art "R-R" based approaches even for data loss rates as high as 30%.

The method and apparatus of the present invention are ideally suited for home based environments where signal fidelity is less reliable when compared to hospital or institutional settings. In particular, it is expected that in a home monitoring setting, patients will be much more mobile thus introducing high amounts of noise. In addition, wireless transmission losses and device buffer overruns can result in time periods where the collected signal is either unusable or just missing. For such settings, an analysis algorithm that is robust to lost data is crucial, because the traditional approaches are easily confused by the lack of data and produce results that have little connection to the true state of the patient.

BRIEF DESCRIPTION OF THE DRAWINGS

The foregoing and other objects, features and advantages of the invention will be apparent from the following more particular description of preferred embodiments of the invention, as illustrated in the accompanying drawings in which like reference characters refer to the same parts throughout the different views. The drawings are not necessarily to scale, emphasis instead being placed upon illustrating the principles of the invention.

DETAILED DESCRIPTION OF THE INVENTION

A description of preferred embodiments of the invention follows.

Figure 1:
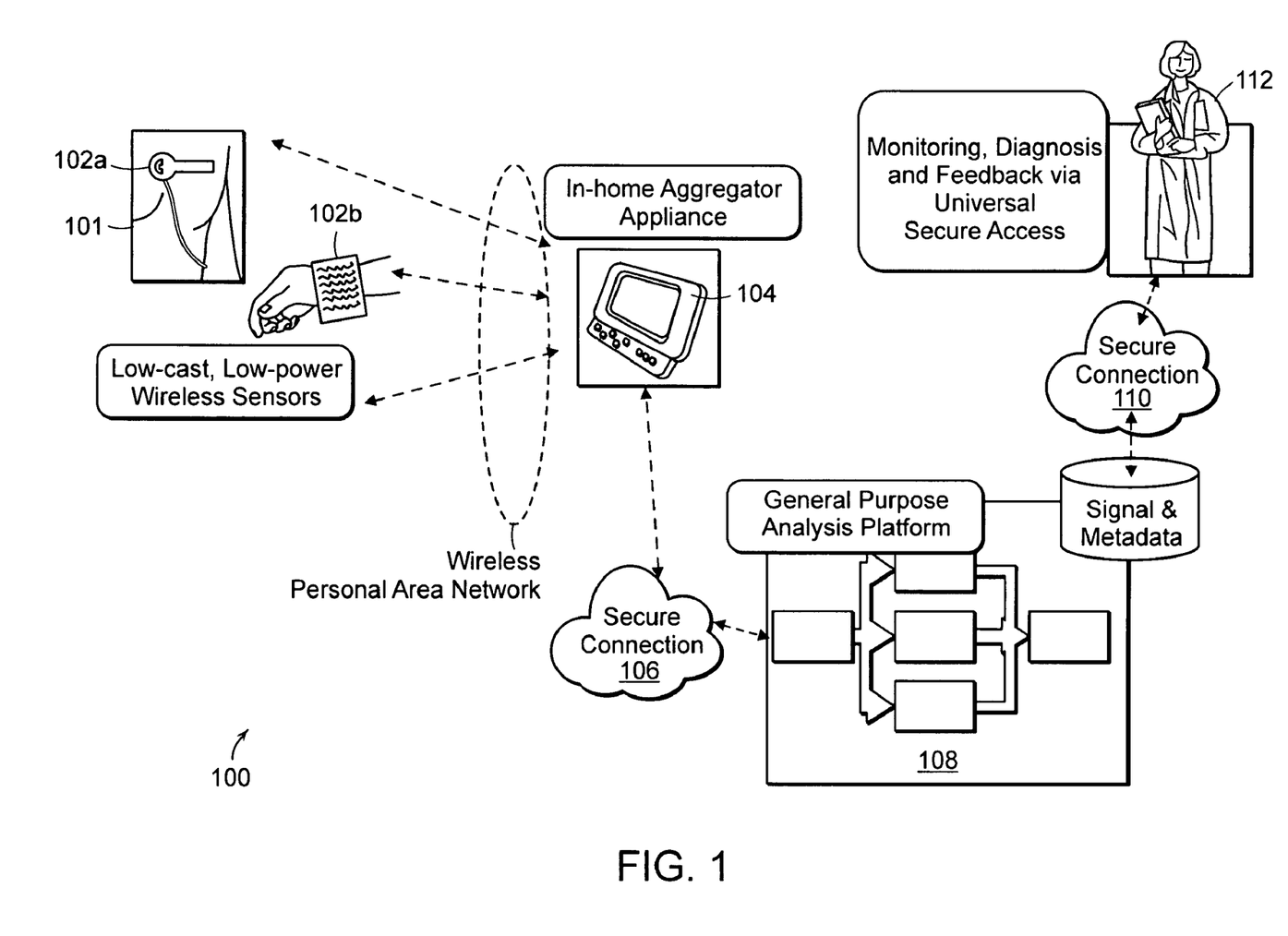
FIG. 1 is a schematic diagram of a continuous monitoring system employing the method and the apparatus of the present invention.

A typical continuous monitoring system is shown in FIG. 1. Patients 101 wear data-collecting devices 102a or 102b that collect data of interest continuously. The data is aggregated by aggregator appliance 104 and transmitted via connection 106 to a remote analysis and archiving platform 108 for further archiving and analysis. Care providers 112 are given secure access to remote analysis and archiving platform 108 over connection 110 so they can monitor their patients 101, receive notifications and/or alerts, and possibly provide feedback to the patients based on the analysis and their own expertise.

Atrial fibrillation is the fluttering of the heart's atria which can result in stagnation of blood flow, blood clots, and eventually stroke. Unfortunately the early stages of the disease are asymptomatic and intermittent and as such can be very difficult to diagnose.

Figure 2A:
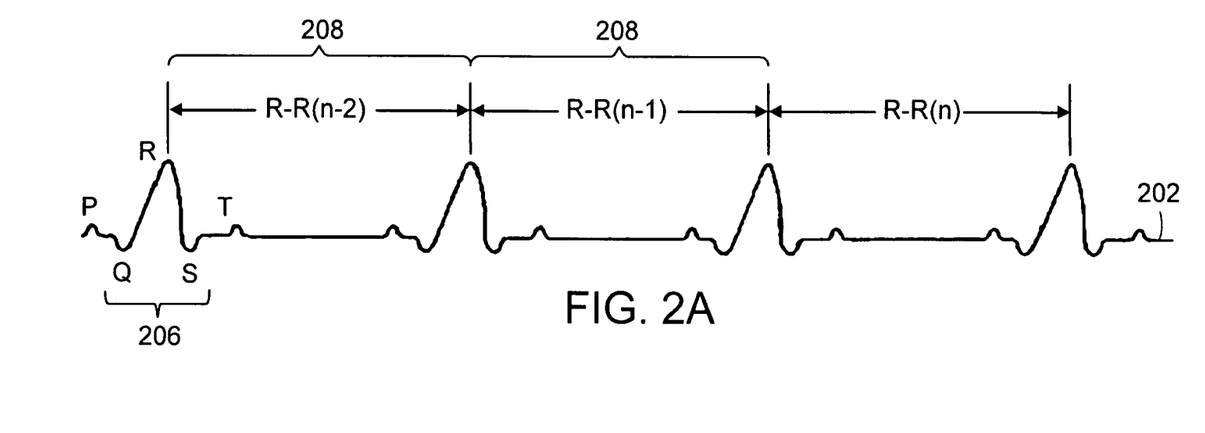
FIG. 2A and FIG. 2B are EKG plots showing cardiac rhythms.
Figure 2B:
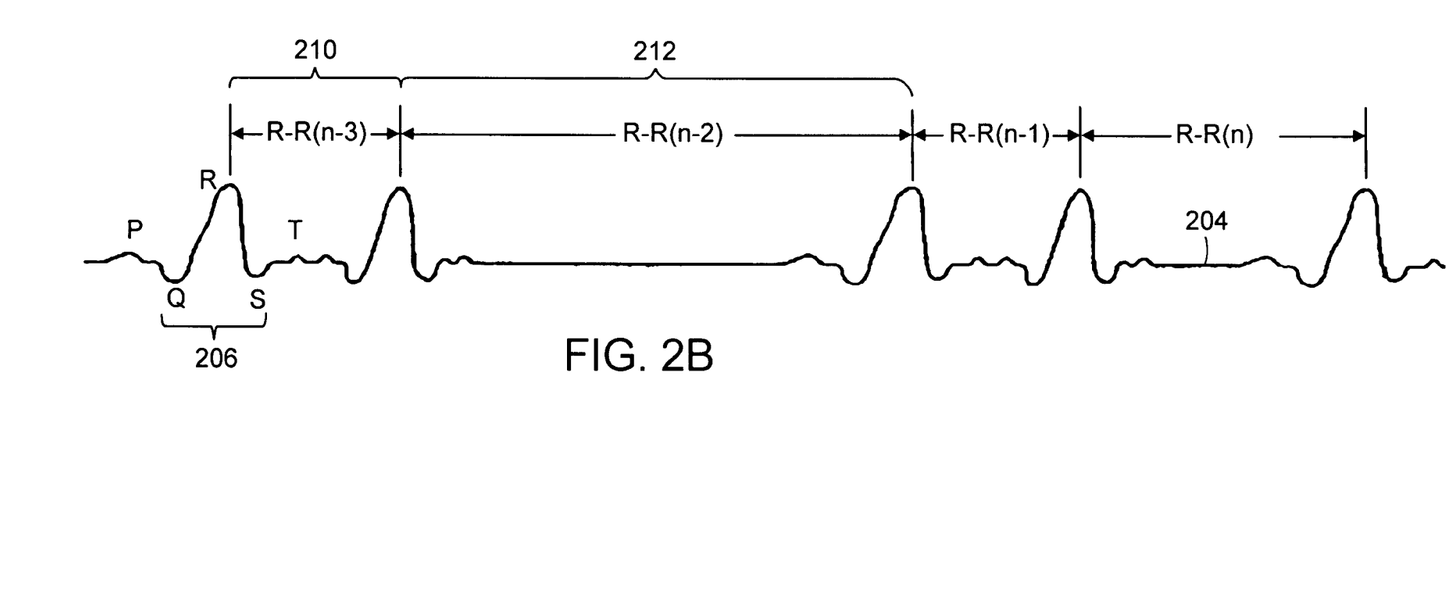

Referring now to FIGS. 2A and 2B, two graphs 202 and 204 of cardiac rhythms are shown. Typical QRS complexes 206 are shown. A "typical" QRS complex includes an atrial "P" component that has a small positive amplitude, about 50 to 100 microvolts, and a relatively short duration of about 40 to 80 milliseconds. Thereafter, following a brief interval of quiescence on the order of about 150 milliseconds, the signal cycles through a "QRS" complex corresponding to depolarization of the cardiac muscle in which the signal swings briefly negative in the "Q" component, then a relatively sharp positive spike of about one millivolt in the "R" component, and thereafter through a brief negative swing in the "S" component. A nominal QRS duration of 100 milliseconds is typical. After another brief quiescent interval on the order of 200 milliseconds, a slight positive swing corresponding to the "T" component indicates repolarization of the cardiac muscle. The interval between cardiac rhythm signals is the inverse of the pulse rate and would be one second, for example, for a typical cardiac rhythm at sixty beats per minute.

In the cardiac rhythm of FIG. 2A, the beats are approximately equally spaced and the R-R intervals 208 will be approximately equal. In the cardiac rhythm of FIG. 2B, the beats are not equally spaced. Two beats are closer to each other than a following beat. The R-R intervals will therefore vary. The R-R interval 210 is shorter than the R-R interval 212.

Typically, atrial fibrillation is detected using either an R-R interval approach, or other signal morphology cues. Even though this discussion focuses of measuring R-R intervals, one skilled in the art will appreciate that any cardiac beat detection method can be adopted for use with the atrial fibrillation event detection method of the present invention. Accordingly, in one embodiment of the present invention, the R-R interval is monitored to detect an atrial fibrillation event.

The method and apparatus of the present invention make it possible to automatically detect atrial fibrillation for mobile patients in a long term continuous monitoring setting, under the conditions of partial data loss. When data fidelity and continuity cannot be assumed at all times, the data analysis algorithm needs to be cognizant of data loss and react accordingly. The method for detecting atrial fibrillation of the present invention addresses these concerns and results in significant accuracy improvements over the traditional Afib detection techniques.

The operation of the method of the present invention will now be described with reference to FIG. 3.

At step 302, the EKG signal is captured. Any EKG device known in the art or other means for detecting and/or recording electrocardiac activity can be used to capture the EKG signal. At step 304, the precise time for each beat is identified. Any means for beat detection can be used, such as an EKG monitor or a digital processor programmed to identify EKG signal morphology, e.g., R-wave in a QRS complex.

At step 306, a gap in the signal is detected and measured. In a preferred embodiment, the EKG signal is sampled at a pre-determined frequency and transmitted in a data stream that comprises time-stamped data packets. In this embodiment, the timestamp information for every incoming EKG packet is detected at step 306. Since the sampling frequency for the EKG signal is known, the expected timestamp for each incoming EKG packet can be calculated and thus missing data can be detected.

At step 308, the inter-beat interval is calculated, for example, the interval between two successive R-waves. Any means for computing time intervals can be used, for example a digital processor programmed to compute time intervals. The computed interval between two detected beats is outputted if the gap in an EKG signal is not more than a pre-determined fraction alpha of the computed interval. Fraction alpha can be from about 1% to about 50%. For example, fraction alpha can be one-half (50%), i.e. should a gap exist and should it overlap the interbeat interval by more than 50% of the interval's distance, the interbeat interval will be discarded. Alternatively, fraction alpha can be smaller (e.g. 5%, 10%, 15%, 25%, 30%, 35%, 40%, or 45%) for higher fidelity results, at the expense of larger periods of uncertainty where it is not known whether the patient had the pathology or not.

At step 310, the variance of outputted inter-beat intervals is computed. The variance is computed for the intervals calculated for a pre-determined number N of detected cardiac beats. Number N can be, for example fifteen or in the range of 12 to 20. Furthermore, the variance of the intervals between cardiac beats is computed only if no interval is greater than a predetermined time T. Time T can be, for example, 2.5 seconds or in the range of 2-5 seconds. Thus, should successive beats be too far apart, the variance computation is started afresh. In any case T should never be larger than 5 seconds before flushing the state and starting afresh.

At step 312, the portions of the EKG signals that include high variance values are classified as atrial fibrillation events, while the portions that include low variance values are classified as normal sinus rhythm.

A method of using inter-beat interval variance for detection of atrial fibrillation events is described, for example, in G. B. Moody and R. Mark, "A new method for detecting atrial fibrillation using r-r intervals", *Computers in Cardiology* 1983, IEEE Computer Society Press (1983), pages 227-230 and in U.S. Pub. Pat. Appl. No. 20050165320. The entire teachings of these publications are incorporated herein by reference. In short, an event is classified as atrial fibrillation if variance of inter-beat intervals, computed either over a pre-determined time or over a pre-determined number of beats, is above a threshold value V. Typically, V is 200 (in units of standard deviation).

At step 314, a smoothing operation is applied to the output provided by the classification step 312 to reduce volatility in the output of the classifier. The smoothing procedure discards portions of the EKG signal classified as atrial fibrillation events if the duration of such portion falls below a pre-determined threshold value S. Threshold value S can be measured in units of time or in numbers of cardiac beats. (See Moody et al. and U.S. Pub. Pat. Appl. No. 20050165320). Preferably, a portion of the EKG signal classified as an atrial fibrillation event is discarded if such portion comprises fewer than a pre-determined number of beats M. Typically, M is about 300.

Thus, the smoothing operation 314 adds some hysteresis to the output of the classifier 312 ensuring that the output of the system stays in a certain state for a minimum amount of time or a number of beats.

At step 316, the annotations are added so that the portions of the EKG signals that include high variance values and that were not discarded at step 314 are classified as atrial fibrillation events, while low variance values are classified as normal sinus rhythm. Thus, atrial fibrillation is detected.

In an alternative embodiment, the smoothing operation 314 looks at the time distance between successive outputs of the variance computing step 310. If the time distance between successive variance outputs is too large, the smoothing operator 314 flushes its internal state and starts the smoothing process from scratch. This prevents the smoothing operator from joining intervals that are far part into one contiguous interval of a particular type because it is preferable to have the diagnosis identify regions of missing information rather than classifying them mistakenly as an atrial fibrillation event or normal sinus rhythm.

Figure 3:
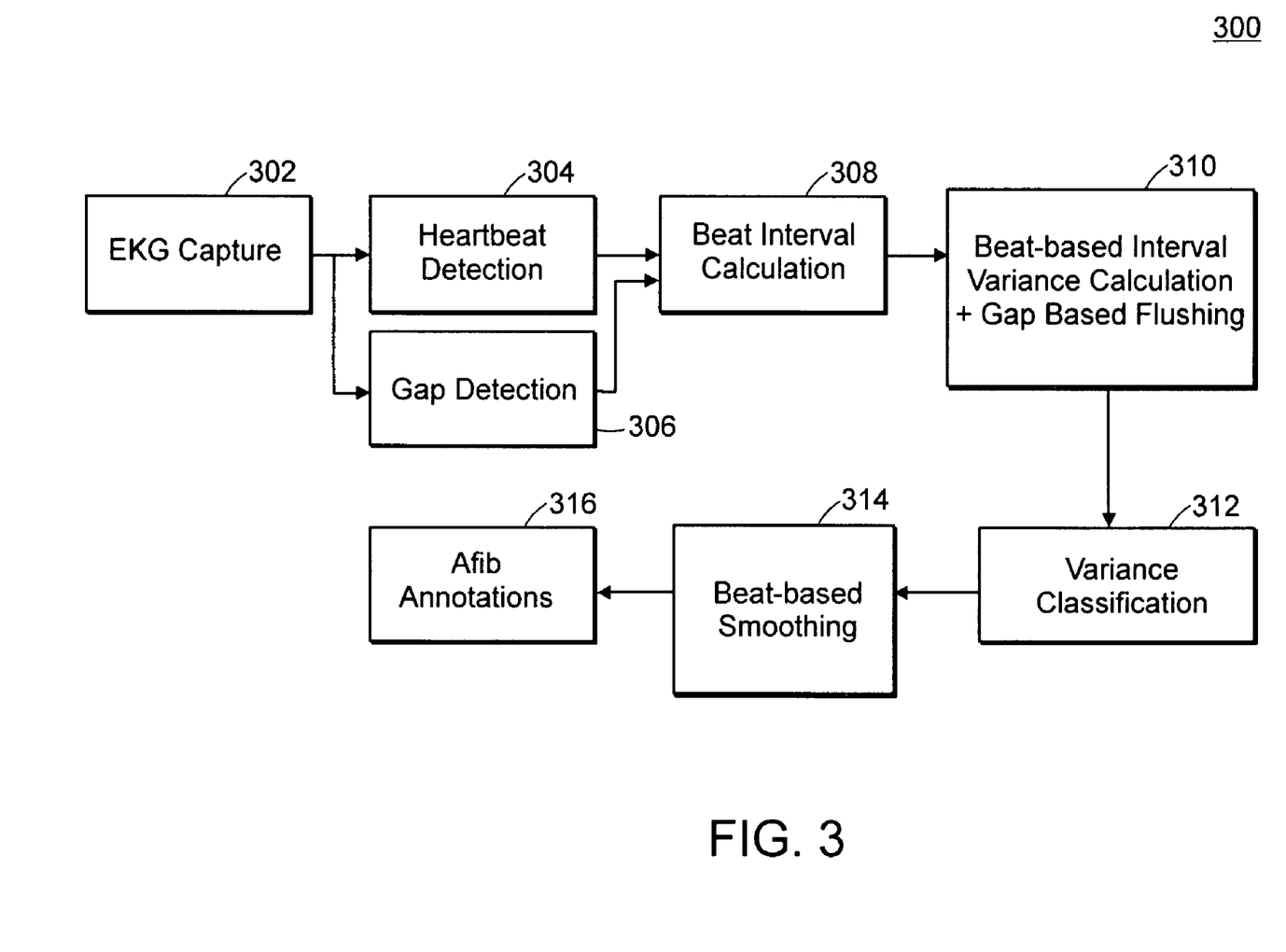
FIG. 3 is a flow-chart showing the steps of the method of the present invention.
Figure 6:
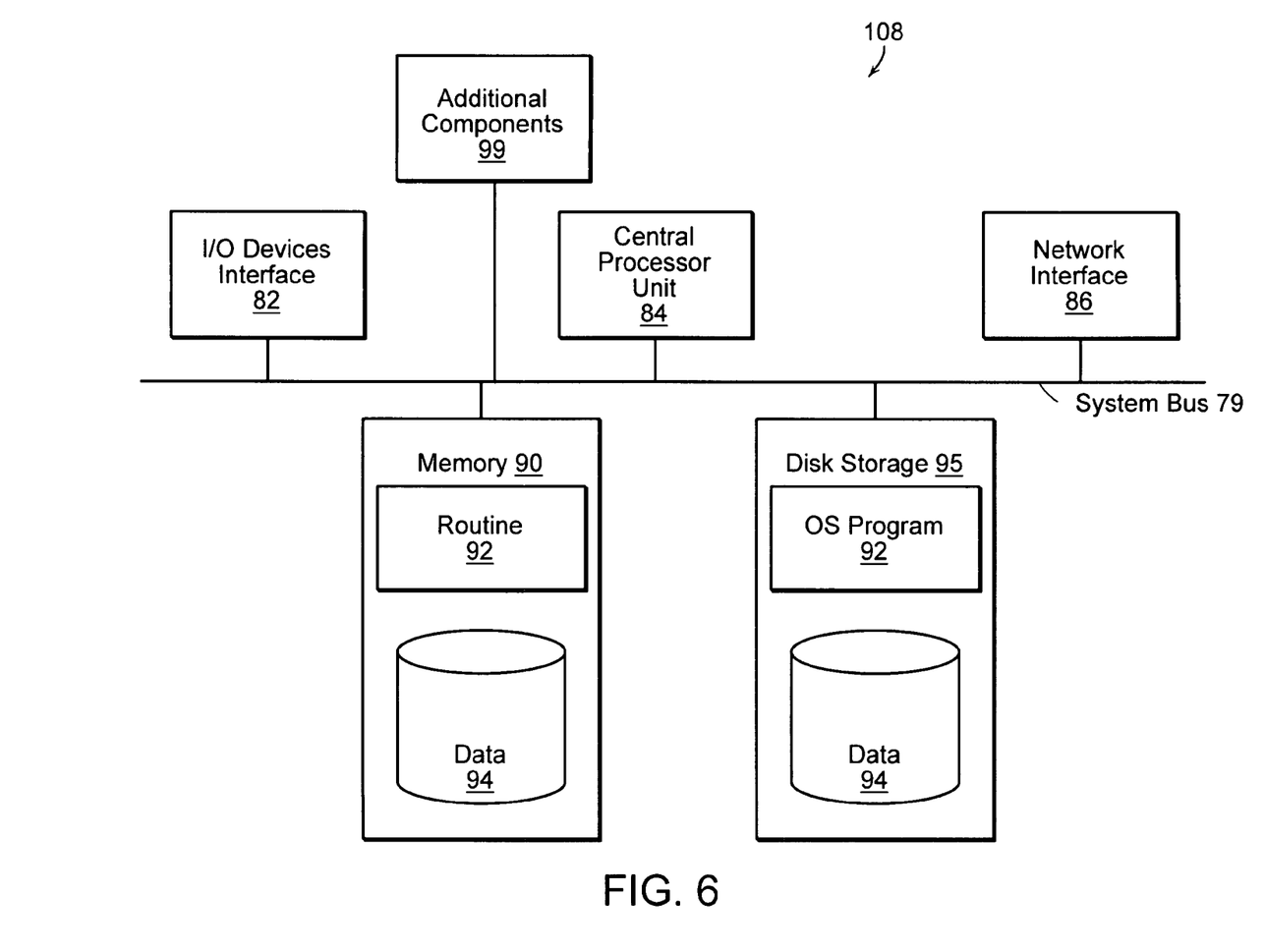
FIG. 6 is a schematic diagram of a computer-implemented system for executing an embodiment of an apparatus of the present invention.

FIG. 6 is a diagram of the internal structure of a portion of analysis and archiving platform 108 (FIG. 1) that can execute the method presented in FIG. 3. Each component of the system depicted in FIG. 6 is connected to system bus 79, where a bus is a set of hardware lines used for data transfer among the components of a computer or processing system. Also connected to bus 79 are other components 99 of platform 108 (see FIG. 1) such as additional memory storage, digital processors, network adapters and I/O device. Bus 79 is essentially a shared conduit that connects different elements of a computer system (e.g., processor, disk storage, memory, input/output ports, network ports, etc.) that enables the transfer of information between the elements. Attached to system bus 79 is I/O device interface 82 for connecting various input and output devices (e.g., keyboard, mouse, displays, printers, speakers, etc.) to remote analysis and archiving platform 108. Network interface 86 allows the computer to connect to various other devices attached to a network (e.g., networks connections 106 and 110 of FIG. 1). Memory 90 provides volatile storage for computer software instructions 92 and data 94 used to implement a method of the present invention. Disk storage 95 provides non-volatile storage for computer software instructions 92 and data 94 used to implement a method of the present invention. Central processor unit 84 is also attached to system bus 79 and provides for the execution of computer instructions.

In one embodiment, the processor routines 92 and data 94 are a computer program product (generally referenced 92), including a computer readable medium (e.g., a removable storage medium such as one or more DVD-ROM's, CD-ROM's, diskettes, tapes, etc.) that provides at least a portion of the software instructions for the invention system. Computer program product 92 can be installed by any suitable software installation procedure, as is well known in the art. In another embodiment, at least a portion of the software instructions may also be downloaded over a cable, communication and/or wireless connection. In other embodiments, the invention programs are a computer program propagated signal product embodied on a propagated signal on a propagation medium (e.g., a radio wave, an infrared wave, a laser wave, a sound wave, or an electrical wave propagated over a global network such as the Internet, or other network(s)). Such carrier medium or signals provide at least a portion of the software instructions for the present invention routines/program 92.

In alternate embodiments, the propagated signal is an analog carrier wave or digital signal carried on the propagated medium. For example, the propagated signal may be a digitized signal propagated over a global network (e.g., the Internet), a telecommunications network, or other network. In one embodiment, the propagated signal is a signal that is transmitted over the propagation medium over a period of time, such as the instructions for a software application sent in packets over a network over a period of milliseconds, seconds, minutes, or longer. In another embodiment, the computer readable medium of computer program product 92 is a propagation medium that analysis and archiving platform 108 may receive and read, such as by receiving the propagation medium and identifying a propagated signal embodied in the propagation medium, as described above for computer program propagated signal product.

Generally speaking, the term "carrier medium" or transient carrier encompasses the foregoing transient signals, propagated signals, propagated medium, storage medium and the like.

Exemplification

Figure 4:
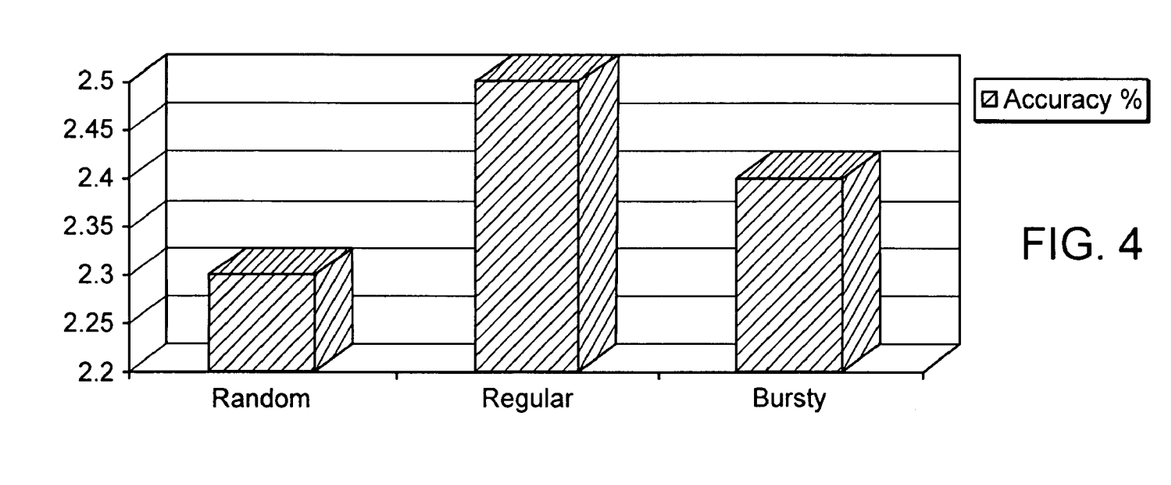
FIG. 4 is a bar plot showing percent accuracy of detecting an artial fibrillation event by a prior method under the conditions of 10% loss of the packets in the data stream. (The labels "random", "regular" and "bursty" refer to the mode of packet loss.)

FIG. 4 is a graph illustrating the accuracy of the atrial fibrillation detection method of prior art on a signal where 10% of all packets are lost and the loss can be random, regular, or bursty. As can be seen accuracy of detection plummets from upwards of 90% to less than 3% even though 90% of all data is still being received.

Figure 5:
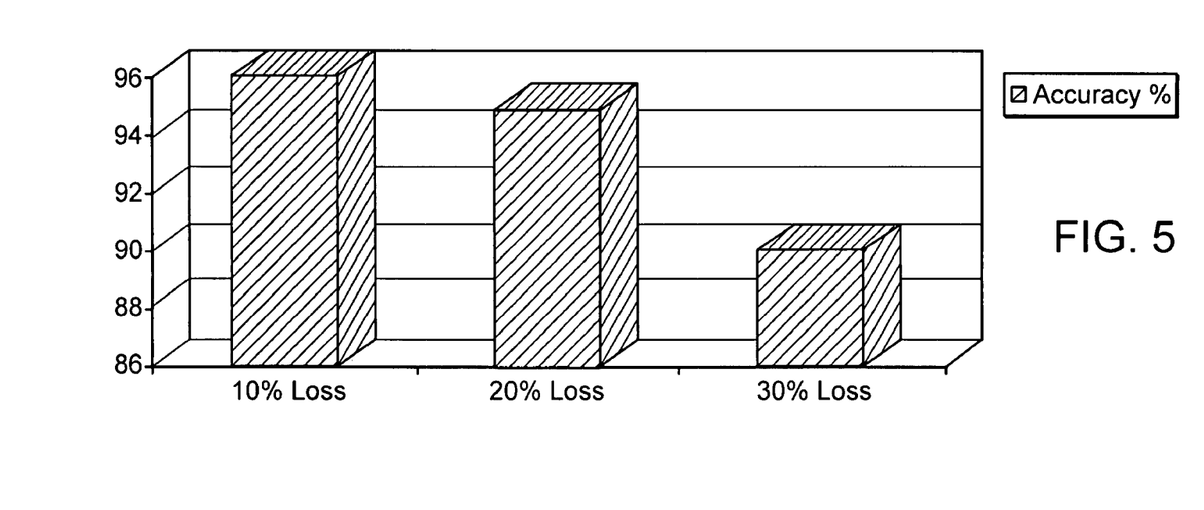
FIG. 5 is a bar plot showing accuracy of detecting an artial fibrillation event by the method of the present invention under the conditions of 10%, 20% and 30% loss of the packets in the data stream.

Referring to FIG. 5, when the method of the present invention is used, data processing is much more robust to packet loss than the prior method and can continue to detect atrial fibrillation events accurately (90% and greater accuracy) even when packet loss is as high as 30%.

EQUIVALENTS

While this invention has been particularly shown and described with references to preferred embodiments thereof, it will be understood by those skilled in the art that various changes in form and details may be made therein without departing from the scope of the invention encompassed by the appended claims.

What is claimed is:

1. A method of detecting a cardiac atrial fibrillation event in a non-continuous electrocardiogram (EKG) signal, the method comprising:
   a) detecting a portion of the EKG signal comprising cardiac beats, wherein the portion includes at least one gap;
   b) measuring a duration of the gap in the detected portion of the EKG signal;
   c) computing a plurality of inter-beat intervals using the cardiac beats, wherein a computed inter-beat interval of the plurality is selected if the measured gap duration in the detected portion of the EKG signal is not more than a fraction alpha of the computed inter-beat interval;
   d) computing a variance of the selected inter-beat intervals;
   e) classifying the portion of the EKG signal as indicative of an atrial fibrillation event if the computed variance of the classified portion of the EKG signal exceeds a pre-determined value V;
   f) discarding the portion of the EKG signal classified as indicative of atrial fibrillation if the classified portion has a duration less than a pre-determined threshold S; and
   g) annotating the EKG signal, a non-discarded portion of the EKG signal having the computed variance that exceeds the pre-determined value V being annotated as an atrial fibrillation event.

2. The method of claim 1, wherein the EKG signal comprises time-stamped packets.

3. The method of claim 2, wherein the gap duration in the EKG signal detected portion is measured by comparing a time-stamp of each time-stamped packet to an expected time-stamp.

4. The method of claim 1, wherein the fraction alpha is about one-half.

5. The method of claim 1, wherein the variance of the selected inter-beat intervals is computed for a pre-determined number of cardiac beats N.

6. The method of claim 5, wherein the variance of the selected inter-beat intervals is computed if no selected inter-beat interval is greater than a predetermined time T.

7. The method of claim 6, wherein the pre-determined number of cardiac beats N equals about 15 and the predetermined time T is not greater than 2.5 seconds.

8. The method of claim 1, wherein the pre-determined threshold S is a number of cardiac beats M.

9. The method of claim 8, wherein the number of cardiac beats M is about 300.

10. A method of detecting a cardiac atrial fibrillation event in a non-continuous electrocardiogram (EKG) signal carried in a data stream that comprises time-stamped packets, the method comprising:
    a) detecting a portion of the data stream carrying the EKG signal comprising cardiac beats, wherein the portion includes at least one gap;
    b) comparing a time-stamp of each time-stamped packet to an expected time-stamp to measure a duration of the gap in the portion of the EKG signal data stream;
    c) computing a plurality of inter-beat intervals, wherein a computed inter-beat interval of the plurality is selected if the measured gap duration in the portion of the EKG signal data stream is not more than a fraction alpha of the computed inter-beat interval;
    d) computing a variance of the selected inter-beat intervals for a predetermined number of cardiac beats N if no selected inter-beat interval is greater than a predetermined time T;
    e) classifying the portion of the EKG signal data stream as indicative of an atrial fibrillation event if the computed variance of the classified portion of the EKG signal data stream exceeds a pre-determined value V;
    f) discarding the portion of the EKG signal data stream classified as indicative of atrial fibrillation if the classified portion has a duration less than a pre-determined number of cardiac beats M; and
    g) annotating the EKG signal data stream, a non-discarded portion of the EKG signal data stream having the computed variance that exceeds the pre-determined value V being annotated as an atrial fibrillation event.

11. The method of claim 10, wherein the fraction alpha is about one-half.

12. The method of claim 11, wherein the predetermined number of cardiac beats N is about 15 and the predetermined time T is not greater than 2.5 seconds.

13. The method of claim 12, wherein the pre-determined number of cardiac beats M is 300.

14. An apparatus that detects a cardiac atrial fibrillation event in a non-continuous electrocardiogram (EKG) signal, the apparatus comprising:
    a) means for detecting a portion of the EKG signal comprising cardiac beats, wherein the portion includes at least one gap;
    b) means for measuring a duration of the gap in the portion of the EKG signal;
    c) means for computing inter-beat intervals that selects a computed interval if the measured gap duration in the portion of the EKG signal is not more than a fraction alpha of the computed inter-beat interval;
    d) means for computing a variance of the selected inter-beat intervals;
    e) means for classifying the portion of the EKG signal as indicative of an atrial fibrillation event if the computed variance of the classified portion of the EKG signal exceeds a pre-determined value V;
    f) means for discarding the portion of the EKG signal classified as indicative of atrial fibrillation if the classified portion has a duration less than a pre-determined threshold S; and
    g) means for annotating the EKG signal, a non-discarded portion of the EKG signal having the computed variance that exceeds the pre-determined value V being annotated as an atrial fibrillation event.

15. The apparatus of claim 14, wherein the EKG signal comprises time-stamped packets.

16. The apparatus of claim 15, wherein the means for measuring a duration of a gap in the portion of the EKG signal comprises means for comparing a time-stamp of each time-stamped packet to an expected time-stamp.

17. The apparatus of claim 14, wherein the means for computing a variance computes the variance of selected inter-beat intervals representing a pre-determined number of cardiac beats N.

18. The apparatus of claim 17, wherein the means for computing a variance computes the variance if no selected inter-beat interval is greater than a predetermined time T.

19. The apparatus of claim 18, wherein the fraction alpha is about one-half.

20. The apparatus of claim 19, wherein the pre-determined number of cardiac beats N is equal to about 15 and the pre-determined time T is not greater than 2.5 seconds.

21. The apparatus of claim 14, wherein the pre-determined threshold S is a number of cardiac beats M.

22. The apparatus of claim 21, wherein the number of cardiac beats M is about 300.

23. An apparatus that detects a cardiac atrial fibrillation event in a non-continuous electrocardiogram (EKG) signal carried in a data stream that comprises time-stamped packets, the apparatus comprising:

a) means for detecting a portion of an EKG signal comprising cardiac beats, wherein the portion includes at least one gap;

b) means for comparing a time-stamp of each time-stamped packet to an expected time-stamp to measure a duration of the gap in the portion of the EKG signal;

c) means for computing inter-beat intervals that selects a computed inter-beat interval if the measured gap duration in the portion of the EKG signal is not more than a fraction alpha of the computed inter-beat interval;

d) means for computing a variance of the computed inter-beat intervals selected by the means for computing inter-beat intervals, the variance being computed for a pre-predetermined number of cardiac beats N, wherein the means for computing a variance computes the variance if no selected inter-beat interval is greater than a predetermined time T;

e) means for classifying the portion of the EKG signal as indicative of an atrial fibrillation event if the computed variance of the portion of the EKG signal exceeds a pre-determined value V;

f) means for discarding the portion of the EKG signal classified as indicative of atrial fibrillation if the classified portion has a duration less than a number of cardiac beats M; and     g) means for annotating the EKG signal, a non-discarded portion of the EKG signal having the computed variance that exceeds V being annotated as an atrial fibrillation event.

24. The apparatus of claim 23, wherein the fraction alpha is about one-half.

25. The apparatus of claim 24, wherein the pre-determined number of cardiac beats N equals about 15 and the predetermined time T is not greater than 2.5 seconds.

26. The apparatus of claim 23, wherein the number of cardiac beats M is about 300.

* * * * *